United States Patent [19]

Gorman et al.

[11] Patent Number: 5,650,324

[45] Date of Patent: *Jul. 22, 1997

[54] INHIBITOR AND ANTI-INHIBITOR MONOCLONAL ANTIBODIES SPECIFIC FOR HORSERADISH PEROXIDASE

[75] Inventors: Kevin Matthew Gorman; John Linforth Daiss, both of Rochester, N.Y.

[73] Assignee: Johnson & Johnson Clinical Diagnostics, Inc., Rochester, N.Y.

[*] Notice: The term of this patent shall not extend beyond the expiration date of Pat. No. 5,565,326.

[21] Appl. No.: 251,496

[22] Filed: May 31, 1994

[51] Int. Cl.$^6$ .............. C07K 16/00; C12P 21/08
[52] U.S. Cl. .............. 530/388.26; 435/7.4; 435/28; 435/172.2; 435/962; 436/512; 436/518; 436/523; 436/531; 436/537; 436/548; 530/388.1
[58] Field of Search .............. 435/7.4, 7.9, 28, 435/962, 172.2, 240.21; 436/512, 518, 523, 531, 537, 548; 530/388.1, 388.26, 807

[56] References Cited

U.S. PATENT DOCUMENTS

| | | | |
|---|---|---|---|
| 4,621,048 | 11/1986 | Ashihara et al. | 435/5 |
| 4,868,109 | 9/1989 | Lansdrop | 435/28 |
| 5,085,988 | 2/1992 | Olson | 435/7.91 |

FOREIGN PATENT DOCUMENTS

| | | |
|---|---|---|
| 0094777 | 11/1983 | European Pat. Off. . |
| 137657 | 4/1985 | European Pat. Off. . |
| 487301 | 5/1992 | European Pat. Off. . |
| 230936 | 9/1983 | Germany . |
| 243185 | 9/1983 | Germany | 530/388.1 |

OTHER PUBLICATIONS

Marucci, Immunochemistry, 10, pp. 278–280, 1973.
Conroy et al, Immunochemistry, 13, pp. 599–603, 1976.
Conroy et al, Molecular Immunology, 19(5), pp. 659–663, 1982.
Conroy et al, Molecular Immunology, 20(6), pp. 647–653, 1983.
Boot et al, J. Immun. Methods, 103, pp. 69–77, 1987.
Tipton, Memphis State University thesis (Ph.D.), Dec., 1988.
Lansdorp et al, Methods in Enzymology, vol. 21, pp. 855–867, 1986.
Kim et al, "Evaluation of dissociation contants of antigen–antibody complexes by ELISA," Journal of Immunological Methods 131 (1990) pp. 213–222.
Tipton et al., "Epitope Mapping of Horseradish Peroxidase with Use of Monoclonal Antibodies," Hybridoma 9(1990): pp. 319–330.
Biological Abstract 88(8):85479 issued 1989.
Chemical Abstract 103(1):4883.
Biological Abstract 98(8):101871.

*Primary Examiner*—Carol A. Spiegel

[57] ABSTRACT

Monoclonal antibodies have been prepared which are of the IgG isotype and are highly specific for horseradish peroxidase. One group of antibodies inhibits at least about 95% of the normal activity of horseradish peroxidase when bound to the enzyme. A second group of antibodies inhibits less than about 20% of the enzymatic activity when bound to the enzyme, but prevents the binding of the antibodies from the first group. The antibodies in either group can be conjugated to specific binding ligands such as drugs or hormones.

17 Claims, No Drawings

INHIBITOR AND ANTI-INHIBITOR MONOCLONAL ANTIBODIES SPECIFIC FOR HORSERADISH PEROXIDASE

FIELD OF THE INVENTION

This invention relates to monoclonal antibodies specific to horseradish peroxidase. In particular, it relates to two types of monoclonal antibodies: those which inhibit the enzyme activity (identified as "inhibitors" herein), and those which prevent the "inhibitor" antibodies from binding to horseradish peroxidase (identified as "anti-inhibitors" herein). This invention also relates to conjugates of such antibodies and to hybridomas from which they are obtained. Such antibodies have a number of uses including their use in diagnostic assays, as described below.

BACKGROUND OF THE INVENTION

Antibodies are normally synthesized by lymphoid cells derived from B lymphocytes in bone marrow. Individual lymphocytes cannot be directly cultured to produce a specific antibody. However, Kohler et al, *Nature* 256, 495 (1975) demonstrated that a process of somatic cell fusion, specifically between a lymphocyte and myeloma cell, could yield hybrid cells which grow in culture and produce a specific antibody. The hybrid is termed a "hybridoma" cell herein and in the art generally. In a typical fusion procedure, spleen lymphocytes from an animal immunized against a chosen antigen are fused with myeloma cells. The resulting hybridomas are then dispersed in a series of separate culture tubes or microtiter plate wells to screen for cultures providing the desired antibody specific to the antigen. Positive cultures are further diluted to obtain colonies arising from a single cell (or clone). The clones are again screened for production of the desired antibody, which is known as a "monoclonal" antibody in the art.

Monoclonal antibodies are highly specific, being directed to a single determinant on a single antigen, unlike the conventional "polyclonal" antibodies containing molecules specific to various determinants of the antigen. Monoclonal antibodies are useful to improve the selectivity and specificity of diagnostic and therapeutic methods using immunological binding. They are also uncontaminated by other immunoglobulins.

While the production of monoclonal antibodies has been known for some time, there remain difficulties in preparing consistently specific antibodies. For any given case, the choice of animal species and myeloma cell line, and the selection technique used for isolating the desired hybridoma cell line are all important to the outcome.

Horseradish peroxidase ($H_2O_2$: donor oxidoreductase, E.C. 1.11.1.7) has been a useful enzyme label in immunological diagnostic and immunohistochemical reactions for many years. Its principle advantages are its high turnover number and its relative lack of substrate specificity, allowing its activity to be expressed by the generation of a variety of colorimetric, electrochemical or chemiluminescent signals. In addition, horseradish peroxidase is relatively stable to surface denaturation, lyophilization and other potentially hazardous conditions of manufacture or storage.

Both polyclonal and monoclonal antibodies specific to horseradish peroxidase have been developed which have various degrees of inhibitory effect on the enzymatic properties of the enzyme (see for example, Marucci, *Immunochemistry*, 10, pages 278–280, 1973; Conroy et al, *Immunochemistry*, 13, pages 599–603, 1976; Conroy et al, *Molecular Immunology* 19(5), pages 659–663, 1982; Conroy et al, *Molecular Immunology* 20(6), pages 647–653, 1983; Boot et al, *J. Immun. Methods*, 103, pages 69–77, 1987; and David A. Tipton, Ph.D. Thesis, Memphis State University, December 1988).

EP-A-0 137 657 (published Apr. 17, 1985) describes the production of monoclonal antibodies specific to horseradish peroxidase which do not interfere with the activity of the enzyme.

There remains a need for "inhibitor" antibodies which shut down substantially all (greater than 95%) of the activity of horseradish peroxidase. There is also a need in antibodies specific to horseradish peroxidase which do not substantially affect enzyme activity but, when bound to the enzyme, completely prevent the binding of inhibiting antibodies to the enzyme.

SUMMARY OF THE INVENTION

The present invention provides a monoclonal antibody having the following characteristics:
  a) specific to horseradish peroxidase,
  b) being of the IgG class,
  c) a dissociation constant less than or equal to about 50 nmolar, and
  d) binds to horseradish peroxidase in such a manner that the enzymatic activity of horseradish peroxidase is diminished by no more than about 20%, and binding of any inhibitor antibody specific to horseradish peroxidase, with horseradish peroxidase is substantially blocked.

This invention also provides hybridoma cell lines from which the monoclonal antibody described above can be produced.

Moreover, a water-soluble conjugate is also provided which is formed from the monoclonal antibody described above and a specific binding ligand.

Also provided by this invention is a second type of monoclonal antibody which has the following characteristics:
  a) specific to horseradish peroxidase,
  b) being of the IgG class,
  c) a dissociation constant less than or equal to about 25 nmolar, and
  d) binds to horseradish peroxidase in such a manner as to inhibit the enzymatic activity of horseradish peroxidase by at least about 95%.

The present invention further provides a water-soluble conjugate formed from the second type of monoclonal antibody described above and a specific binding ligand.

Yet again, this invention also provides a hybridoma cell line from which the second type of monoclonal antibody described above can be produced.

We have found monoclonal antibodies specific only to horseradish peroxidase which have highly desired properties. One class of these antibodies, identified herein as "anti-inhibitor" antibodies, do not inhibit enzymatic activity, but prevent the binding to the enzyme by those that do inhibit the enzymatic activity (identified as "inhibitor" antibodies herein). Both types of antibodies can be used to advantage in various immunological and immunohistochemical methods. In particular, they can be used to advantage in specific binding assays which are defined in more detail in copending and commonly assigned U.S. Ser. No. 08/250883 (filed on even date herewith) by Daiss, Gorman and Hinchman, and entitled "Separation-Free Specific Binding Assays Using Anti-Inhibitor Antibodies".

These antibodies have a single specificity. That is, they are not bispecific or reactive with more than one ligand.

DETAILED DESCRIPTION OF THE INVENTION

As used herein, the term "monoclonal antibody" includes whole immunoglobulin molecules having the single specificity as is conventional in the art. In addition the term is intended to include chemically prepared fragments [such as Fab, F(ab)', F(ab)$_2$ fragments] of such molecules and genetically prepared equivalents thereof (such as "single chain antibody fragments" or ScFv fragments).

The monoclonal antibodies of this invention have various uses in diagnostic and therapeutic techniques. These can include the detection, identification or localization of specific antigens, receptors and cell surface sites and other uses which would be readily apparent to one skilled in the art.

Generally, the monoclonal antibodies are prepared by immunizing a suitable mammal (such as a mouse or rat) with native horseradish peroxidase (Servac Corporation, Capetown, South Africa), or with the enzyme conjugated to carrier proteins such as mouse IgG (Jackson Immunoresearch, West Grove, Pa.) or C-reactive protein (Scripps, La Jolla, Calif.), following the conventional procedures described by Kohler et al, supra. For example, each immunization can be with 100 µg of enzyme or conjugate in MPL® +TDM Emulsion (MPL is a registered trademark of RIBI Immunochem Research, Inc., Hamilton, Mont., and stands for Monophosphoryl Lipid A Immunostimulant; TDM stands for trehalose dicorynomycolate) per mouse every five weeks. A final booster immunization containing antigen in phosphate buffered saline solution was given 4 to 5 days before hybridoma fusion.

A population of splenocytes from the immunized animals can be washed in Dulbecco's modified Eagle's medium (DMEM) containing 10% fetal bovine serum, suspended for five minutes in a lysing buffer (155 mmolar ammonium chloride, 10 mmolar potassium bicarbonate and 0.1 molar ethylenediaminetetraacetic acid), and washed again two times with serum-free DMEM. Fusion with suitable hybridoma cell lines can be accomplished in the presence of polyethylene glycol (PEG1450) or another fusogen following the teaching of Lane [*J. Immunolo Methods* 81, pages 223–228 (1985)]. The resulting hybridized cells are then diluted into selective media, distributed into microtiter plates and cultured for 7 to 21 days before screening to see what type of properties the antibodies possess.

A variety of myeloma cell lines are commercially available for hybridization with the mammalian spleen cells. Sources of such cell lines include the American Type Culture Collection (ATCC) in Rockville, Md. Particularly useful myeloma cell lines include the Sp2/0-Ag14 and P3×63Ag8.653 myeloma cell lines, both available from the ATCC. The first cell line is preferred.

Screening for antibody production is a critical step in hybridoma technology. The hybridoma culture supernatants described above can be screened by three independent assays. The first assay enables one to choose antibodies which are specific to horseradish peroxidase using conventional Enzyme Linked Immunosorbent Assays (ELISA) in polystyrene microtiter plates containing adsorbed horseradish peroxidase conjugate.

Specificity for Horseradish Peroxidase:

A sample (50 µl/plate well) of each culture supernate is placed in a microtiter well coated with a conjugate of horseradish peroxidase and an irrelevant antibody which served to mediate the adsorption of horseradish peroxidase to the microtiter plate. This antibody can be obtained, for example, from Jackson Immunoresearch. After a 30–60 minute incubation, the plates are washed with a suitable buffered solution of a nonionic surfactant, and the presence of mouse or rat horseradish peroxidase specific monoclonal antibodies is detected with a conjugate of anti-mouse IgG or anti-rat IgG and alkaline phosphatase (conjugate with anti-mouse Fc obtained, for example, from Jackson Immunoresearch). A dye signal can be generated by adding the substrate p-nitrophenyl phosphate disodium salt (4 mg/ml) in tris(hydroxymethyl)aminomethane buffer (1.5 molar, pH 8). Other signal producing reagents (such as other substrates), or other enzyme labels can be similarly used. The screened antibodies which provide a dye signal after about 30 minutes which is at least twice as dense as a background signal are considered to be specific for horseradish peroxidase. The dye signal can be measured using a conventional microtiter plate reader or spectrophotometer.

Antibodies specific to horseradish peroxidase can be screened for inhibitory function as follows:

Assay for Enzyme Inhibition:

A sample (50 µl) of each culture supernate is placed in a microtiter plate well, followed by addition of a solution (50 µl) of horseradish peroxidase (0.2 nmolar) and gelatin (0.8%) in phosphate buffered saline, and the resulting mixtures are allowed to stand for 10 minutes at room temperature. Residual enzyme activity is then determined by adding 100 µl of the horseradish peroxidase substrate, o-phenylenediamine (1 mg/ml), in citrate/phosphate buffer (50 mmolar, pH 5.5), and measuring the amount of dye signal at 450 nm using a conventional microplate reader which had been adapted for kinetics. Other substrates, or dye providing reagents can be similarly used.

Those culture supernates that inhibit horseradish peroxidase by more than about 20% (compared to a control without the presence of monoclonal antibody) are considered for further investigation as inhibitor antibodies.

The antibodies evaluated in this manner are subjected to further evaluation to find those which are within the scope of the present invention, namely those that inhibit horseradish peroxidase activity by at least about 95% compared to the signal provided by the enzyme in the absence of the antibodies. This evaluation was carried out by the procedure described above.

Antibodies specific to horseradish peroxidase are also screened for their ability to inhibit the binding of inhibitor antibodies to the enzyme.

Assay for Anti-Inhibition

A sample (25 µl) of horseradish peroxidase (0.4 nmolar) is added to each well of a microtiter plate, followed by addition of a sample (50 µl) of each culture supernate, incubated 30 minutes, followed by addition of the inhibitor monoclonal antibody 4-22.2 (25 µl, 15 nmolar, defined below in Table I). After a 10 minute incubation, substrate solution (100 µl) is added and the dye signal from peroxidase activity is evaluated as described above (that is, using o-phenylenediamine as substrate). Anti-inhibitor antibodies within the scope of this invention are defined as those which block the inhibition of horseradish peroxidase by the inhibitor antibody 4-22.2 described herein. Generally, the inhibitor antibody is added at a level sufficient to inhibit 80–90% of enzymatic activity, and more than 30% of the enzymatic activity is measured upon coincubation with an anti-inhibitor antibody.

When used to modify the percent of enzymatic activity inhibition in the disclosure and claims, the term "about"

refers to a variation of ±5%. When used to modify the $K_d$ values herein, the term "about" refers to a variation of ±50%.

In the preparation of monoclonal antibodies of this invention, selected hybridomas were cloned in soft agar and individual clones were plucked, cultured using conventional means and screened using the procedures described above. Monoclonal antibodies were grown in shaker flasks, and the antibodies collected and purified using conventional affinity chromatography on either immobilized Protein A or Protein G. Other conventional purification procedures can be used if desired.

The dissociation constants ($K_d$) for inhibitor antibodies were determined by measuring the concentration of the antibody required to inhibit 50% of horseradish peroxidase activity (as compared to enzymatic activity in the absence of antibody). The inhibitor antibodies of this invention generally have a $K_d$ less than or equal to 25 nmolar, preferably a $K_d$ less than or equal to 1 nmolar, and more preferably a $K_d$ less than or equal to 0.5 nmolar.

The $K_d$ values for anti-inhibitor antibodies were determined by measuring the concentration of antibody required to prevent 50% of the inhibition of 0.1 nmolar horseradish peroxidase by 10 nmolar of inhibitor antibody 4-22.2 (defined below in Table I) which was determined to inhibit about 99% of the enzymatic activity as defined above. These $K_d$ values are generally less than or equal to 50 nmolar, preferably less than or equal to 25 nmolar and more preferably less than or equal to 5 nmolar. Preferably, these antibodies diminish the activity of horseradish peroxidase by no more than 6%.

It should be understood that these $K_d$ values are relative measures for the antibodies, and that alternative methods for measuring that parameter may give higher or lower values.

All of the monoclonal antibodies of this invention are of the IgG class. Determination of isotype of cloned antibody cultures is achieved using conventional isotyping assays and test kits which are commercially available. Horseradish peroxidase can be immobilized on various supports, directly or indirectly, for the isotyping assays.

The following Table I lists representative useful inhibitor monoclonal antibodies of this invention by species of origin, isotype, $K_d$ and maximum horseradish peroxidase inhibition:

TABLE I

| Antibody | Species/Isotype | Kd (n molar) | Max. Inhibition (%) |
| --- | --- | --- | --- |
| 4-22.2 | rat*/IgG1 | 0.14 | 99 |
| 3-8.1 | mouse**/IgG2a | 25 | 97 |

*Sprague-Dawley rats
**Swiss/Webster mice

The 4-22.2 monoclonal antibody identified above is preferred. It is prepared using the novel hybridoma cell line identified herein as HB 11603 which has been deposited with the ATCC under the Budapest Treaty.

The following Table II lists useful anti-inhibitor monoclonal antibodies of this invention by species of origin, isotype, $K_d$ and maximum horseradish peroxidase inhibition:

TABLE II

| Antibody | Species/Isotype | Kd (n molar) | Max. Inhibition (%) |
| --- | --- | --- | --- |
| 7-32.2 | mouse/IgG2a | 3.3 | 0 |
| 6-89.1 | rat*/IgG2a | 3.5 | 6 |
| 6-82.1 | rat*/IgG2a | 7.0 | 10 |
| 6-71.2 | rat*/IgG2a | 10 | 8 |
| 6-55.2 | rat*/IgG1 | 20 | 6 |

*Sprague-Dawley rats

The 7-32.2 monoclonal antibody is preferred. It is prepared using the novel hybridoma cell line identified herein as HB 11604 which has been deposited with the ATCC under the Budapest Treaty. The 6-89.1 monoclonal antibody is prepared using a novel hybridoma cell line identified herein as HB 11635 which has also been deposited with the ATCC under the Budapest Treaty.

The anti-inhibitor antibodies of this invention can be used to prepare various water-soluble conjugates for use in various diagnostic and therapeutic procedures, such as competitive binding immunoassays, and other assay protocols as described in more detail in the copending U.S. Ser. No. 08/250883 of Daiss, Gorman and Hinchman, identified above.

One such conjugate is a reaction product of the anti-inhibitor antibody and a specific binding ligand. The conjugate can be prepared using any conventional technique of the art for covalently binding proteins with other proteins, hormones, drugs or other chemical compounds having requisite reactive groups. Thus, the various reactive groups of the antibodies and ligand can be considered in choosing the means for making the conjugate, such groups including, but are not limited to, carboxy, amino, hydroxy, thiol and imidazole groups. Useful methods of binding include, but are not limited to, binding of peptides, periodate oxidation, use of glutaraldehyde, carbodiimides or N-hydroxysuccinimide, and others readily apparent to one skilled in the art. Details for each of these and other methods are found in voluminous literature, including Williams et al *Methods in Immunology and Immunochimistry*, Academic Press, New York, 1976, and Yoshitake et al, *Eur. J. Biochem.* 101, 395 (1979).

Such ligands can include any material which is capable of specifically binding with a receptor molecule, such as an antibody, and can include antibiotics, drugs, hormones, peptides, proteins, carbohydrates, and other materials readily apparent to one skilled in the art. Particularly useful specific binding ligand includes compounds having a molecular weight below about 1600 daltons, such as various therapeutic drugs, drugs of abuse, antibiotics and what are known as surrogate antigens (or peptides which behave like antigenic proteins). Specific ligands are vancomycin, digoxin, phenobarbital, diphenylhydantoin and prostaglandin $E_2$.

Water-soluble conjugates of the inhibitor antibodies of this invention and specific binding ligands can similarly be prepared.

The following examples are provided for illustrative purposes only, and the scope of the invention is not to be construed as limited thereto. Unless otherwise noted, the percentages are by weight.

EXAMPLE 1

Preparation of Inhibitor Monoclonal Antibody Specific to Horseradish Peroxidase

The monoclonal antibody identified above as 4-22.2 in Table I was prepared using hybridoma cell line HB 11603 (ATCC) as follows:

Sprague-Dawley rats were injected with a solution of horseradish peroxidase (400 µg) in commercially available TDM/MPL emulsion adjuvant (RIBI Corporation) four times at four week intervals. A fifth and final injection was made with horseradish peroxidase (400 µg) in phosphate buffered saline solution. Three days later, splenocytes from the immunized rats were fused with cells from the Sp2/0-Ag14 myeloma cell line using conventional procedures.

Screening of the resulting antibodies for specificity to horseradish peroxidase was carried out as described above by adding 50 µl of the culture supernate to the wells of a microtiter plate coated with a conjugate of horseradish peroxidase and an irrelevant antibody which served to mediate the adsorption of the enzyme to the microtiter plate. The bound antibody was detected by adding a conjugate of alkaline phosphatase with goat anti-mouse IgG Fc (Jackson Immunoresearch), followed by signal generation using 4 mg/ml p-nitrophenyl phosphate disodium salt (Sigma Chemical) as substrate for the alkaline phosphatase in tris (hydroxymethyl)aminomethane buffer (1.5 molar, pH 8). The dye signal was evaluated after 30 minutes using a conventional microtiterplate reader.

Screening for horseradish peroxidase inhibitory function was carried out by adding a sample (50 µl) of each culture supernatant to microtiter plate wells, followed by addition of horseradish peroxidase (0.2 nmolar) and gelatin (0.8%) in phosphate buffered saline solution, and the resulting mixtures were allowed to stand for 10 minutes at room temperature. Residual activity was then determined by adding 100 µl of o-phenylenediamine (1 mg/ml) in citrate/phosphate buffer (50 µl, 50 mmolar, pH 5.5), and measuring the dye signal at 450 using a microtiter reader adapted for kinetics.

Those antibodies which inhibited the enzymatic activity by at least 20% were selected by adding equal volumes of the culture supernate and horseradish peroxidase to microtiter plate wells and using the procedure described above ("Assay for Enzyme Inhibition"). Antibody 4-22.2 was determined to inhibit horseradish peroxidase activity at least 99%.

EXAMPLE 2

Preparation of Anti-Inhibitor Monoclonal Antibody Specific to Horseradish Peroxidase The monoclonal antibody identified above as 6-89.1 in Table II was prepared using hybridoma cell line HB 11635 (ATCC) as follows:

Immunization of rats and fusion of the resulting splenocytes were carried out as described in Example 1. Screening for horseradish peroxidase activity was carried out as described in Example 1 except that after the plates were shaken for 10–30 minutes, a solution (25 µl) of the inhibitor antibody 4-22.2 (about 15 nmolar, described above) was added to each plate well. The resulting mixtures were allowed to incubate for 10 minutes at room temperature.

Residual horseradish peroxidase activity was determined by adding a solution (100 µl) of o-phenylenediamine (1.2 mg/ml) in citrate/phosphate buffer (0.1 molar, pH 5.5), and measuring the amount of dye signal at 450 nm using a conventional spectrophoto-meter as described in Example 1.

The determination of the antibody which is an anti-inhibitor was carried out using the procedure described above ("Assay for Anti-Inhibition"). Antibody 6-89.1 was determined to diminish enzyme activity by only 6%.

Antibody 7-32.2 (Table II) was similarly prepared using hybridoma cell line HB 11604 (ATCC).

EXAMPLE 3

Preparation of Conjugates of Anti-Inhibitor Monoclonal Antibody and Diphenylhydantoin Hapten Water-soluble conjugates of a diphenylhydantoin hapten and two anti-inhibitor monoclonal antibodies of this invention were prepared. This preparation is representative only, and is not essential to preparing conjugates of the present invention. Alternative preparatory methods also exist.

The hapten, 5,5-diphenyl-3-{4-[4-(3-succinimidoxycarbonylpropionyl)-1-piperazinylcarbonyl]-butyl}-2,4-imidazolidinedione, was prepared by procedures described in Preparatory Example 2 of EP-A-0 517 327 (published May 5, 1993).

This hapten was conjugated to the monoclonal antibodies identified as 7-32.3 or 6-89.1 (Table II) in either a 9:1 or 18:1 molar ratio by adding concentrated hapten in dimethyl sulfoxide slowly, dropwise to a solution of either antibody (1 mg/ml) in N-[2-hydroxyethyl]piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

EXAMPLE 4

Preparation Of Conjugates of Anti-Inhibitor Monoclonal Antibody and Phenobarbital Hapten Two water-soluble conjugates of a phenobarbital hapten and anti-inhibitor monoclonal antibodies of this invention were prepared in the following manner. This preparation is representative only, and is not essential to preparing conjugates of the present invention. Alternative preparatory methods also exist.

The hapten, 5-ethyl-5-phenyl-1-{4-[4-(3-succinimidoxycarbonylpropionyl)-1-piperazinylcarbonyl]-butyl}-2,4,6-(1H, 3H, 5H)pyrimidinetrione, was prepared by procedures described in Preparatory Example 4 of EP-A-0 517 327 (published May 5, 1993).

This hapten was conjugated to the monoclonal antibodies identified as 7-32.3 or 6-89.1 (Table II) in either a 9:1, 18:1 or 27:1 molar ratio by adding concentrated hapten in dimethyl sulfoxide slowly, dropwise to a solution of either antibody (1 mg/ml) in N-[2-hydroxyethyl]piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

EXAMPLE 5

Preparation of Conjugates of Anti-Inhibitor Monoclonal Antibody and Digoxin Hapten Two water-soluble conjugates of a digoxin hapten and anti-inhibitor monoclonal antibodies of this invention was prepared in the following manner. This preparation is representative, as other methods for making such conjugates can be used.

Hapten was conjugated to the monoclonal antibodies identified as 7-32.3 or 6-89.1 (Table II) by diluting 2 mg of each antibody 1:1 with sodium acetate (0.1 molar, pH 5.5), not to exceed 2 ml. Sodium metaperiodate (1 ml) was added at 6.66 mg/ml. The reaction mixture was covered with foil and rotated for 20 minutes at room temperature. Excess sodium metaperiodate was removed by passing the reaction mixture over a commercially available PD10 column (Pharmacia, Inc.) and preequilibrated with sodium acetate (0.1 molar, pH 5.5). To vials (3 mg in 1 ml) of digoxigenin-x-hydrazide (Boehringer Mannheim) was added to each mixture and incubated for 1 hour at room temperature. To block reaction, excess glycine (final concentration of 10%) was added at pH 7, followed by sodium cyanoborohydride in water to a final concentration of 20 mmolar. The reaction mixture was stirred for 3 hours at room temperature, then dialyzed overnight into 3-(N-morpholino)propanesulfonic acid (0.02 molar, pH 7) buffer. The final product conjugates were filtered through a commercially available 0.22 μmeter filter (Nalge Corporation, Rochester, N.Y.). The final protein concentration was determined by absorbance at 280 nm using a commercially available spectrophotometer (Beckman Instruments).

The invention has been described in detail with particular reference to preferred embodiments thereof, but it will be understood that variations and modifications can be effected within the spirit and scope of the invention.

We claim:

1. A monoclonal antibody having the following characteristics:
   a) specifically binds to horseradish peroxidase,
   b) an IgG class antibody,
   c) a dissociation constant less than or equal to about 20 nmolar, and
   d) specifically binds to said horseradish peroxidase in such a manner that enzymatic activity of said horseradish peroxidase is diminished by no more than about 20%, and wherein said binding of said monoclonal antibody to said horseradish peroxidase prevents any inhibitor antibody capable of specifically binding to said horseradish peroxidase from binding to said horseradish peroxidase.

2. The antibody of claim 1 wherein the dissociation constant is less than or equal to about 5 nmolar, and which specifically binds to said horseradish peroxidase in such a manner that the enzymatic activity of said horseradish peroxidase is diminished by no more than about 6%.

3. A hybridoma cell line from which the antibody of claim 1 is produced.

4. The hybridoma cell line of claim 3 having ATCC accession number HB 11604 or HB 11635.

5. A water-soluble conjugate of a specific binding ligand and a monoclonal antibody, said monoclonal antibody having the following characteristics:
   a) specifically binds to horseradish peroxidase,
   b) an IgG class antibody,
   c) a dissociation constant less than or equal to about 50 nmolar, and
   d) specifically binds to said horseradish peroxidase in such a manner that enzymatic activity of said horseradish peroxidase is diminished by no more than about 20%, and wherein said binding of said monoclonal antibody to said horseradish peroxidase prevents any inhibitor antibody capable of specifically binding to said horseradish peroxidase from binding to said horseradish peroxidase.

6. The water-soluble conjugate of claim 5 wherein the dissociation constant of the monoclonal antibody is less than or equal to about 25 nmolar.

7. The water-soluble conjugate of claim 6 wherein the dissociation constant of the monoclonal antibody is less than or equal to about 5 nmolar, and the monoclonal antibody specifically binds to said horseradish peroxidase in such a manner that the enzymatic activity of said horseradish peroxidase is diminished by no more than about 6%.

8. The conjugate of claim 5 wherein said specific binding ligand is vancomycin, digoxin, phenobarbital, diphenylhydantoin or prostaglandin $E_2$.

9. A monoclonal antibody having the following characteristics:
   a) specifically binds to horseradish peroxidase,
   b) an IgG class antibody,
   c) a dissociation constant less than or equal to about 25 nmolar, and
   d) specifically binds to said horseradish peroxidase in such a manner as to inhibit enzymatic activity of said horseradish peroxidase by at least about 95%.

10. The antibody of claim 9 wherein the dissociation constant is less than or equal to about 1 nmolar.

11. The antibody of claim 9 wherein the dissociation constant is less than or equal to about 0.5 nmolar.

12. A hybridoma cell line from which the antibody of claim 9 produced.

13. The hybridoma cell line of claim 12 having ATCC accession number HB 11603.

14. A water-soluble conjugate of a specific binding ligand and a monoclonal antibody, said monoclonal antibody having the following characteristics:
   a) specifically binds to horseradish peroxidase,
   b) an IgG class antibody,
   c) a dissociation constant less than or equal to about 25 nmolar, and
   d) specifically binds to said horseradish peroxidase in such a manner as to inhibit enzymatic activity of said horseradish peroxidase by at least about 95%.

15. The water-soluble conjugate of claim 14 wherein the dissociation constant of the monoclonal antibody is less than or equal to about 1 nmolar.

16. The water-soluble conjugate of claim 14 wherein the dissociation constant of the monoclonal antibody is less than or equal to about 0.5 nmolar.

17. The conjugate of claim 14 wherein said specific binding ligand is vancomycin, digoxin, phenobarbital, diphenylhydantoin or prostaglandin $E_2$.

* * * * *